(12) United States Patent
Kwon et al.

(10) Patent No.: US 10,013,647 B2
(45) Date of Patent: Jul. 3, 2018

(54) METHOD FOR MAGNETICALLY CONTROLLING A MAGNETIC STRUCTURE

(75) Inventors: Sunghoon Kwon, Seoul (KR); Howon Lee, Seoul (KR); Junhoi Kim, Seoul (KR); Ji Yun Kim, Gunpo-si (KR)

(73) Assignee: QUANTAMATRIX INC., Seoul (KR)

(*) Notice: Subject to any disclaimer, the term of this patent is extended or adjusted under 35 U.S.C. 154(b) by 195 days.

(21) Appl. No.: 13/637,467

(22) PCT Filed: Mar. 31, 2011

(86) PCT No.: PCT/KR2011/002239
§ 371 (c)(1),
(2), (4) Date: Dec. 17, 2012

(87) PCT Pub. No.: WO2011/122883
PCT Pub. Date: Oct. 6, 2011

(65) Prior Publication Data
US 2013/0105581 A1 May 2, 2013

(30) Foreign Application Priority Data
Mar. 31, 2010 (KR) .................. 10-2010-0029614

(51) Int. Cl.
*G06K 19/06* (2006.01)
*B01J 19/00* (2006.01)
(Continued)

(52) U.S. Cl.
CPC .... *G06K 19/06196* (2013.01); *B01J 19/0046* (2013.01); *B01L 3/502761* (2013.01); *B03C 1/034* (2013.01); *B03C 1/288* (2013.01); *G01N 33/54346* (2013.01); *G01N 33/587* (2013.01); *G06K 7/08* (2013.01); *G06K 19/022* (2013.01); *B01J 2219/005* (2013.01); *B01J 2219/00317* (2013.01); *B01J 2219/00466* (2013.01);
(Continued)

(58) Field of Classification Search
None
See application file for complete search history.

(56) References Cited

U.S. PATENT DOCUMENTS

| 5,801,472 A | 9/1998 | Wada et al. |
| 5,945,898 A | 8/1999 | Judy et al. |

(Continued)

FOREIGN PATENT DOCUMENTS

| KR | 10-2008-0091955 A | 10/2008 |
| KR | 10-2010-0070095 A | 6/2010 |
| WO | WO2009/017525 | * 2/2009 |

OTHER PUBLICATIONS

H. Lee et al., Bio-Chemical Reaction Enhancement Using Magnetic Axis Controlled Spinning Microparticles With Structural Color Barcode, 14th International Conference on Miniaturized Systems for Chemistry and Life Sciences, Oct. 3-7, 2010.
(Continued)

*Primary Examiner* — Betty J Forman
(74) *Attorney, Agent, or Firm* — STIP Law Group, LLC

(57) ABSTRACT

Provided is a method of magnetically controlling a magnetic structure, the method including: providing a solution containing magnetic structures, each including a magnetic axis in which magnetic nanoparticles are arranged; and controlling movements of the magnetic structures by applying an external magnetic field to the solution.

8 Claims, 11 Drawing Sheets

(51) Int. Cl.
*B01L 3/00* (2006.01)
*G01N 33/543* (2006.01)
*G01N 33/58* (2006.01)
*G06K 7/08* (2006.01)
*G06K 19/02* (2006.01)
*B03C 1/034* (2006.01)
*B03C 1/28* (2006.01)
*G01N 35/00* (2006.01)

(52) U.S. Cl.
CPC ............... *B01J 2219/00468* (2013.01); *B01J 2219/00533* (2013.01); *B01J 2219/00545* (2013.01); *B01J 2219/00549* (2013.01); *B01J 2219/00576* (2013.01); *B01J 2219/00585* (2013.01); *B01J 2219/00596* (2013.01); *B01J 2219/00648* (2013.01); *B01J 2219/00655* (2013.01); *B01L 2200/0668* (2013.01); *B01L 2300/0819* (2013.01); *B01L 2300/0822* (2013.01); *B01L 2400/043* (2013.01); *B03C 2201/18* (2013.01); *B03C 2201/24* (2013.01); *B03C 2201/26* (2013.01); *G01N 35/0098* (2013.01)

(56) References Cited

U.S. PATENT DOCUMENTS

| | | |
|---|---|---|
| 6,794,965 B2 | 9/2004 | Shen et al. |
| 7,362,889 B2 | 4/2008 | Dubowsky et al. |
| 7,435,485 B2 | 10/2008 | Ng et al. |
| 7,489,433 B2 | 2/2009 | Urey et al. |
| 2002/0149466 A1 | 10/2002 | Sunshine |
| 2003/0059823 A1* | 3/2003 | Matsunaga et al. ............... 435/6 |
| 2007/0190640 A1* | 8/2007 | Bangert et al. ............ 435/287.2 |
| 2008/0011977 A1* | 1/2008 | Atwood .................. 252/62.51 R |
| 2008/0176216 A1* | 7/2008 | Doyle et al. ...................... 435/5 |
| 2011/0151377 A1 | 6/2011 | Gray et al. |

OTHER PUBLICATIONS

Li Zhang et al., Artificial bacterial flagella: Fabrication and magnetic control, Applied Physics Letters 94, 064107 (2009), 2009 American Institute of Physics.

Yutaka Nagaoka, et al., Dynamics of disklike clusters formed in a magnetorheological fluid under a rotational magnetic field, Physical Review E 71, 032502 (2005).

Laure K. Lagorce et al., Magnetic Microactuators Based on Polymer Magnets, IEEE Journal of Microelectromechanical Systems, vol. 8, No. 1, Mar. 1999.

Jack W. Judy et al., Magnetically Actuated, Addressable Microstructures, Journal of Microelectromechanical Systems, vol. 6, No. 3, Sep. 1997.

Jianping Ge et al., Magnetochromatic Microspheres: Rotating Photonic Crystals, JACS Articles, Jun. 15, 2009, American Chemical Society.

C. Wilhelm et al., Rotational magnetic particles microrheology: The Maxwellian case, Physical Review E 67, 011504 (2003), The American Physical Society.

Hyoki Kim et al., Structural colour printing using a magnetically tunable and lithographically fixable photonic crystal, Nature Photonics, Sep. 2009, pp. 534-540, vol. 3.

Sonia Melle et al., Structure and dynamics of magnetorheological fluids in rotating magnetic fields, Physical Review E, Apr. 2000, pp. 4111-4117, vol. 61, No. 4.

Manfred Albrecht et al., Magnetic multilayers on nanospheres, Nature Materials 4, 2005, pp. 203-206.

* cited by examiner even in United States Patent

METHOD FOR MAGNETICALLY CONTROLLING A MAGNETIC STRUCTURE

CROSS REFERENCE TO PRIOR APPLICATIONS

This application is a National Stage Patent Application of PCT International Patent Application No. PCT/KR2011/002239 (filed on Mar. 31, 2011) under 35 U.S.C. § 371, which claims priority to Korean Patent Application No. 10-2010-0029614 (filed on Mar. 31, 2010), which are all hereby incorporated by reference in their entirety.

TECHNICAL FIELD

The present disclosure relates to a method of magnetically controlling a magnetic structure.

BACKGROUND

A multiplexed analysis method based on encoded particles is being highlighted in the field of high efficiency bio-molecular detection such as new drug development and clinical diagnosis, owing to its extendability and fast reaction. The multiplexed analysis method may be realized by mixing a lot of encoded probe particles in a vial containing the target analysis object.

It is necessary to use many distinguishable codes in order to obtain high analyzing efficiency for various samples. In order to ensure a sufficient number of codes, a spectral coding method using quantum dots or phosphors and a graphical coding method based on patterning of optically measurable elements on surfaces of microparticles have been suggested.

However, according to the spectral coding method, there are problems regarding handling of various materials for realizing codes, such as overlapping of spectrums, limited number of materials, expensive costs, and limitation in precise controlling of loading of an indicator material of a small amount. In addition, in the case of the graphical coding method such as a binary barcode, there is a limitation in resolution, and accordingly, a wider area is necessary in order to realize a sufficient number of codes, and the number of codes is limited by the sizes of particles. Therefore, a multi-level coding method using binary or greater codes has been suggested; however, the above method has very complicated processes and it is necessary to precisely load a plurality of indicator materials like in the spectral coding method.

Also, a method of appropriately handling microparticles is necessary in order to read codes in the multiplexed analysis method based on encoded particles. For example, it is not easy to selectively isolate the microparticles from a mixture solution.

DISCLOSURE OF THE INVENTION

According to an aspect of the present invention, there is provided a method of magnetically controlling a magnetic structure, the method including: providing a solution containing magnetic structures, each including a magnetic axis in which magnetic nanoparticles are arranged; and controlling movements of the magnetic structures by applying an external magnetic field to the solution.

The movements may include rotation of the magnetic structure due to a magnetic torque of the magnetic axis, or movement of the magnetic structure by a force applied in a direction in which density of the external magnetic force becomes dense.

Probe molecules may exist on a surface of the magnetic structure, and the magnetic structure may be rotated according to rotation of the external magnetic field to accelerate reaction between the probe molecules and target molecules in the solution.

According to another aspect of the present invention, there is provided a method of magnetically controlling a magnetic structure, the method including: inducing a solution containing magnetic structures that are color-coded by arranging magnetic nanoparticles into a container; and collecting the magnetic structures that are color-coded on a wall surface of the container by applying an external magnetic field to the solution; and analyzing information of color codes, wherein surfaces of the magnetic structures, on which the color codes are located, may be arranged two-dimensionally with respect to the wall surface of the container.

According to another aspect of the present invention, there is provided a magnetic structure including: a solid matrix; and a magnetic axis fixed in the solid matrix, wherein the magnetic axis may have a structure in which magnetic nanoparticles are arranged in an axial direction with predetermined intervals therebetween, and the magnetic structure may be moved by a magnetic torque of the magnetic axis according to variation in an external magnetic field.

Probe molecules may be immobilized on a surface of the solid matrix.

According to another aspect of the present invention, there is provided a magnetic structure including: a solid matrix; a first region located on a portion of the solid matrix and including a fixed magnetic axis; and a second region located on another portion of the solid matrix to be connected to the first region, and including a fixed magnetic axis, wherein the magnetic axis of the first region and the magnetic axis of the second region may be oriented in different directions from each other, and the first region and the second region may move differently from each other by heterogeneous magnetic anisotropy of the magnetic axis of the first region and the magnetic axis of the second region when an external magnetic field is applied.

At least a portion of the solid matrix may be fixed on an external material.

According to another aspect of the present invention, there is provided a method of magnetically controlling a magnetic structure, the method including: forming an emulsion by dispersing a composition of magnetic nanoparticles dispersed in a curable medium in an immiscible solvent; fabricating a magnetic structure of a microsphere shape including a magnetic axis by applying a magnetic field, and irradiating light to the emulsion; immobilizing probe molecules on a surface of the magnetic structure; mixing the magnetic structure in a solvent containing target molecules; and accelerating reaction between the probe molecules and the target molecules by rotating or moving the magnetic structure on which the probe molecules are immobilized by applying an external magnetic field.

The method may further include isolating the magnetic structure from the solvent by applying an external magnetic field having an inclined intensity to the solvent after the reaction.

According to another aspect of the present invention, there is provided a device for magnetically controlling a magnetic structure, the device including: a first material supply unit configured to supply a magnetic structure that includes probe molecules and is color-coded by arranging magnetic nanoparticles; a second material supply unit configured to supply a solution containing target molecules; a material mixing unit in which the magnetic structure and the solution are mixed so that the probe molecules and the target molecules react with each other; and a magnetic field application unit configured to apply a magnetic field to the solution so as to rotate or move the magnetic structure in the solution.

The device may further include a decoder configured to observe and decode the magnetic structure on which the probe molecules and the target molecules are combined with each other.

BEST MODE FOR CARRYING OUT THE INVENTION

Figure 1:
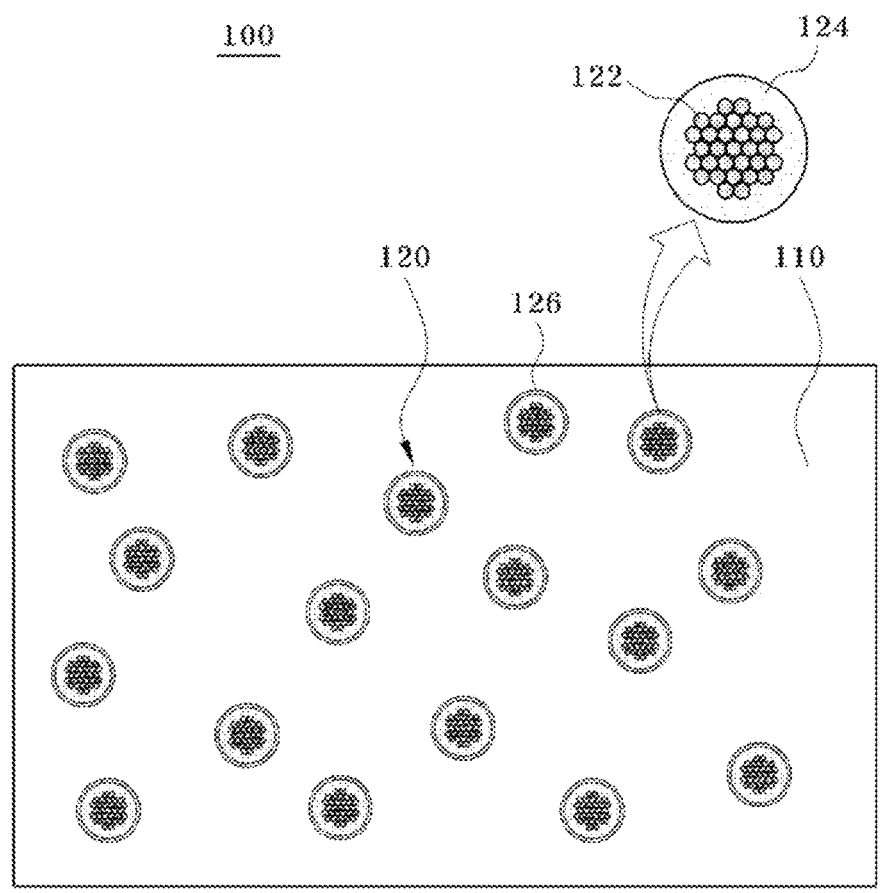
FIG. 1 is a diagram showing an embodiment of a composition for color encoding.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. The drawings are described from a viewpoint of an observer, and it will also be understood that when a layer is referred to as being "on" another layer or substrate, it can be directly on the other layer or substrate, or intervening layers may also be present.

According to an embodiment, color encoding may be performed in the following way: First, a composition including a liquid medium and magnetic nanoparticles dispersed in the liquid medium is provided. The liquid medium may be a curable material. In addition, the magnetic nanoparticles may include a super-paramagnetic material. Next, a magnetic field is applied to the composition so as to arrange the magnetic nanoparticles. At the same time, the composition is hardened by irradiating patterned energy source to the composition. Here, a plurality of portions of the composition are sequentially hardened while changing the intensity of the magnetic field to fix a plurality of color regions, thereby fabricating a color-coded structure. The patterned energy source for performing the curing may include heat, ultraviolet (UV) rays, visible rays, infrared rays, and an electron beam, and is not limited thereto.

Irradiation of patterned UV rays may be performed by a digital micromirror device (DMD).

The one-dimensional chain structure may be formed by arranging the magnetic nanoparticles, and the color of the structure may be determined according to intervals between the magnetic nanoparticles forming the chain structure.

For example, patterned UV rays may be irradiated by using a mask in order to apply the patterned energy source. A technique such as optofluidic maskless lithography (OFML) may be used in order to generate micro-scale patterns of high resolution and to prevent free radicals from dispersing during polymerization.

FIG. 1 is a diagram showing an exemplary embodiment of a composition for color encoding. Referring to FIG. 1, the composition 100 for color encoding may include a curable material 110 and magnetic nanoparticles 120 dispersed in the curable material 110.

The magnetic nanoparticles 120 may include a cluster 122 of magnetic nanocrystals. The size of the magnetic nanoparticles 120 may be several tens to hundreds of nanometers, and the size of the magnetic nanocrystals may be several to several tens of nanometers. Examples of the magnetic nanocrystals may include a magnetic materials or a magnetic alloys. The magnetic material or magnetic alloy may include at least one element selected from the group consisting of Co, $Fe_2O_3$, $Fe_3O_4$, $CoFe_2O_4$, MnO, $MnFe_2O_4$, CoCu, CoPt, FePt, CoSm, NiFe and NiFeCo.

The magnetic nanoparticles 120 may include a superparamagnetic material. The superparamagnetic material has magnetism only in the presence of an external magnetic field, unlike a ferromagnetic material in which magnetism can be maintained without a magnetic field. Usually, when the particle size of a ferromagnetic material is several to several hundreds of nanometers, the ferromagnetic material may be phase-changed into a superparamagnetic material. For example, when iron oxide is in the size of approximately 10 nm, it may have superparamagnetism.

In addition, the magnetic nanoparticles 120 may be, as shown in FIG. 1, coated with a shell layer 124 surrounding a core formed in the cluster 122 of magnetic nanocrystals. The shell layer 124 allows the magnetic nanoparticles 120 to be evenly distributed in the curable material 110. Furthermore, to be described later, the shell layer 124 may stimulate solvation repulsion on a surface of each magnetic nanoparticle 120 to offset potent magnetic attraction between the magnetic nanoparticles 120. For example, the shell layer 124 may include silica. When the shell layer 124 is surface-modified with silica, a known sol-gel process may be used.

In addition, the composition 100 for color encoding may further include a hydrogen bonding solvent. As the hydrogen bonding solvent, various alkanol solvents such as ethanol, isopropyl alcohol and ethylene glycol may be used. Also, a solvation layer 126 surrounding the magnetic nanoparticle 120 may be formed. For example, as the solvation layer 126 is formed due to an influence of a silanol (Si—OH) functional group on a surface of the shell layer 124 having silica, a repulsion force between the magnetic nanoparticles 120 may be induced. According to one exemplary embodiment, the shell layer 124 and/or the solvation layer 126 may not be present on the magnetic nanoparticles 120. In this case, an electrostatic force on the surface of the magnetic nanoparticles 120 may act as a repulsion force.

As the magnetic nanoparticles 120 are mixed with the curable material 110 and subjected to mechanical stirring or ultrasonic treatment, the composition for color encoding 100 may be prepared. The magnetic nanoparticles 120 may be included in the curable material 110 at a volume fraction of, for example, 0.01% to 20%. When the volume fraction of the magnetic nanoparticles 120 is less than 0.01%, reflectivity may be decreased, and when the volume fraction of the magnetic nanoparticles 120 is more than 20%, reflectivity may not be increased any more.

The curable material 110 may serve as a dispersion medium stably dispersing the magnetic nanoparticles 120 forming a photonic crystal. In addition, as the inter-particle distance between the magnetic nanoparticles 120 is fixed by crosslinking of the curable material 110, a certain structural color may be continuously maintained after a magnetic field is eliminated.

The curable material 110 may include a liquid-phase material such as a monomer or an oligomer having a crosslinkable site for curing reaction. The curable material 110 may include a liquid-phase hydrophilic polymer capable of forming a hydrogel. A hydrophilic polymer is a polymer suitable for dispersing the magnetic nanoparticles 120 due to its hydrophilic groups. When the hydrophilic polymer is crosslinked by an appropriate energy source, thereby forming a hydrogel having a three-dimensional network structure, the magnetic nanoparticles 120 may be fixed.

Examples of the curable material 110 capable of forming a hydrogel may include a silicon-containing polymer, polyacrylamide, polyethylene oxide, polyethylene glycol diacrylate, polypropylene glycol diacrylate, polyvinylpyrrolidone, polyvinyl alcohol, polyacrylate or a copolymer thereof. For example, since the curable material 110, polyethylene glycol diacrylate (PEG-DA), has an acrylate functional group at both terminal ends of polyethylene glycol (PEG), the curable material 110 may be crosslinked into a three-dimensional hydrogel via free radical polymerization. The curable material 110 may further include any type of medium which can be changed into a solid from a liquid.

The curable material 110 may further include an initiator, and the initiator may induce free radical polymerization by an external energy source. The initiator may be an azo-based compound or a peroxide. The curable material 110 may further include a proper crosslinking agent, for example, N,N'-methylenebisacrylamide, methylenebismethacrylamide, ethylene glycol dimethacrylate, etc. The magnetic nanoparticles 120 may be aligned in the curable material 110 to generate structural colors under an external magnetic field.

Figure 2:
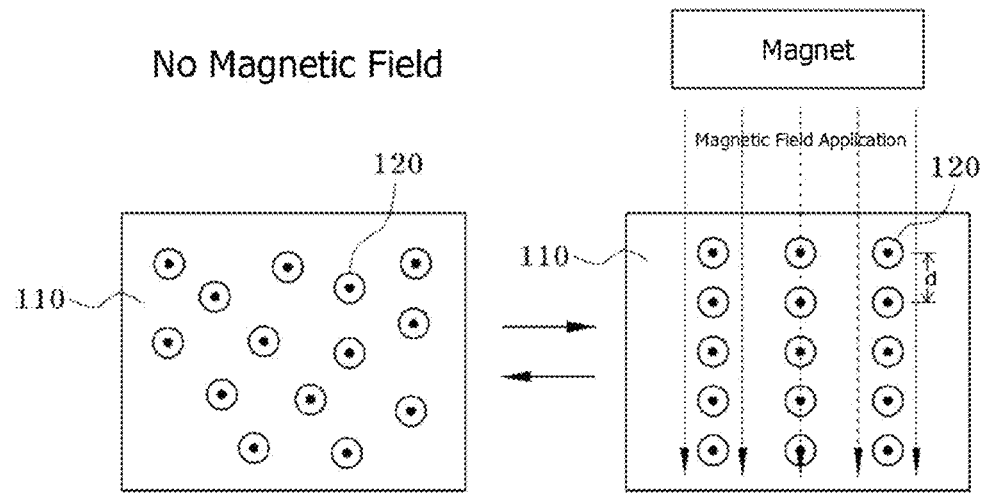
FIG. 2 is a diagram illustrating a principle of arranging magnetic nanoparticles according to a direction of a magnetic field.

FIG. 2 is a diagram showing a principle of arranging magnetic nanoparticles according to a direction of a magnetic field. When a magnetic field is applied to magnetic nanoparticles 120 that are randomly dispersed in a curable material 110 by an adjacent magnet, the magnetic nanoparticles 120 are arranged in parallel with a direction of the magnetic field to form a chain-shaped structure having directivity. The magnetic nanoparticles 120 that are arranged by the magnetic field may return to a non-arranged state when the magnetic field is removed. When a magnetic field is applied to the magnetic nanoparticles 120 existing in a colloid state from outside, attractive force may be applied between the magnetic nanoparticles 120 existing in the curable material 110, and at the same time, repulsive force caused by electrostatic force and salvation force may be applied between the magnetic nanoparticles 120. The magnetic nanoparticles 120 are arranged in a magnetic field direction due to equilibrium between the attractive force and the repulsive force to form a magnetic axis. A magnetic axis denotes a spatial axis representing the strongest induced magnetization in a unit volume. One magnetic nanoparticle 120 forms induced magnetization according to permeability when it is exposed to the magnetic field. Each of the magnetic nanoparticles 120 is likely to be arranged in a direction in which energy of a system is minimum as a result of interaction between induced magnetic moments. Such a direction is parallel with the magnetic field direction, and becomes a magnetic axis.

The distance d between the magnetic nanoparticles 120 forming the magnetic axis may depend on the intensity of the magnetic field. For example, as the intensity of the magnetic field becomes stronger, the distance d between the magnetic nanoparticles 120 that are arranged according to the magnetic field direction may be reduced. The distance d may be a few nm to hundreds of nm according to the intensity of the magnetic field. That is, since a lattice spacing of a photonic crystal varies, a wavelength of reflected light may be changed according to Bragg's Law. Thus, the wavelength of the reflected light may be determined according to the intensity of the magnetic field. Unlike conventional photonic crystals that are reflected at a predetermined wavelength only, the above photonic crystal may show an optical response that is fast, wide, and reversible with respect to an external magnetic field. Reflected light of a variable wavelength may be induced from the external incident light by varying the lattice spacing depending on variation of the peripheral magnetic field.

According to an embodiment of the present invention, a magnetic structure including a magnetic axis is provided. Here, the magnetic axis is fixed in a solid matrix. The magnetic axis has a structure in which magnetic nanoparticles are arranged in an axial direction with predetermined intervals therebetween. Here, when an external magnetic field is applied to the magnetic structure, the magnetic axis is forced to be arranged in parallel with a direction of magnetic force lines. As an example, when an external magnetic field is applied to the magnetic structure, the magnetic structure may be rotated so that the magnetic axis may be arranged in parallel with a direction of magnetic force lines.

Figure 3:
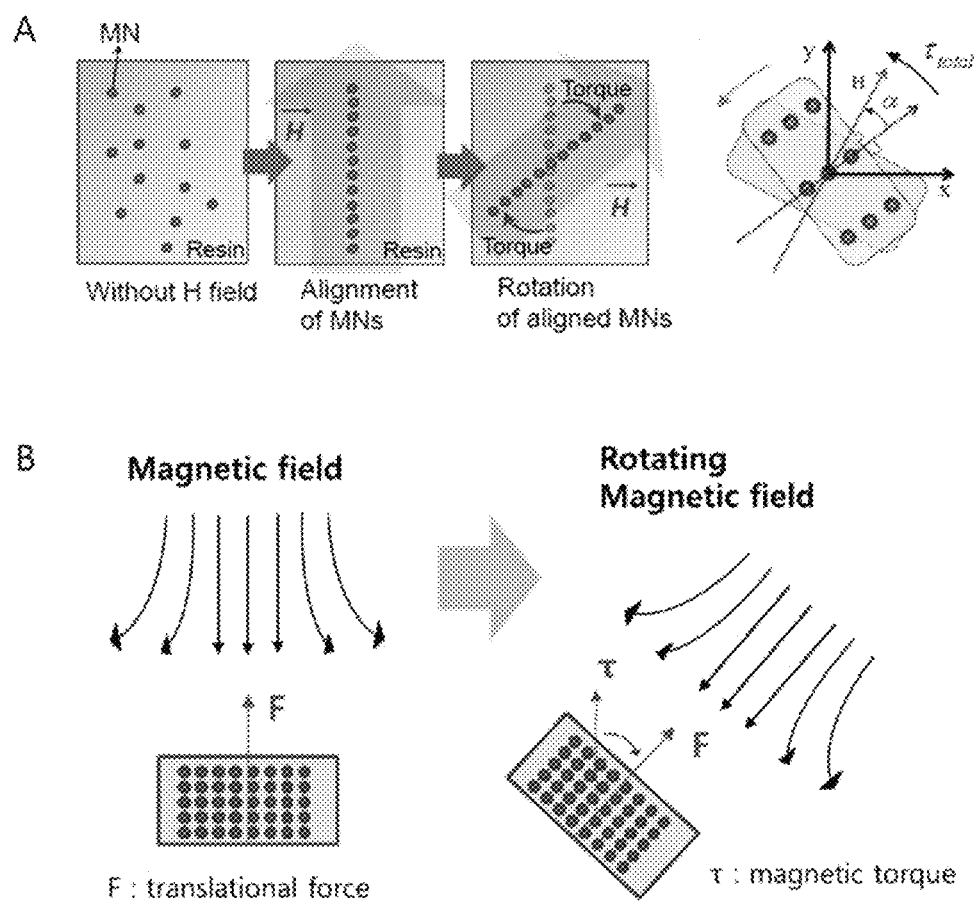
FIGS. 3A and 3B are diagrams showing kinds and principles of forces applied to a magnetic axis including magnetic nanoparticles that are arranged.

FIGS. 3A and 3B are diagrams showing kinds and principles of the forces applied to the magnetic axis including the magnetic nanoparticles that are arranged. FIG. 3A is a diagram showing a characteristic of the magnetic nanoparticles being arranged along an external magnetic field when the magnetic nanoparticles are disposed under a circumstance where the external magnetic field is applied, and FIG. 3B shows two kinds of forces applied to a structure having a magnetic axis when the structure is placed under a circumstance where an external magnetic field that is not completely uniform is applied. Totally, the magnetic nanoparticles have the lowest magnetic energy when the magnetic nanoparticles are arranged along a direction of the external magnetic field, and are in a stable state. In this state, when the direction of the external magnetic field is changed, the magnetic axis is inclined to rotate according to the changed direction in order to reduce entire magnetic energy, and accordingly, magnetic rotating force is generated. When N number of chains exist in one magnetic structure, total magnetic torque ($\tau$ total) is N times greater than a torque ($\tau$ i) of each single chain, and may be represented by following equation. Here, rotating force of a microparticle is represented by following equation:

$$\tau_{total} = N\tau_i = N\frac{3\mu_0 m^2}{4\pi}\sin(2\alpha)\frac{n^2}{d^3} = N\frac{4\mu_0 n^2 \chi^2 R^6 \pi}{3d^3}H^2\sin(2\alpha)$$

Here, N denotes the number of chain structures included in one magnetic structure, $\chi$ denotes initial mass susceptibility of a super-paramagnetic nanoparticle, R is a radius of the super-paramagnetic nanoparticle, d denotes a distance between particles, and n denotes the number of super-paramagnetic particles existing in a single chain. In addition, $\mu_0$ denotes permeability under a vacuum state, m denotes susceptibility of a magnetic nanoparticle, and H denotes intensity of the external magnetic field. $\alpha$ denotes an angle formed by the magnetic axis of the microparticle and an external magnetic force line during rotation. The maximum torque value is shown when the angle $\alpha$ is 45°.

At the same time, if the external magnetic field is not completely uniform, force for dragging the magnetic nanoparticles in a direction in which density of the external magnetic field becomes dense, that is, translational force is applied to the magnetic nanoparticles due to magnetic properties thereof. The above force ($F_m$) may be represented by following equation:

$$\vec{F}_m = V_p \frac{1}{\mu_0}(\chi_p - \chi_f)(\vec{B}\cdot\nabla)\vec{B}$$

Here, $V_p$ denotes the volume of a microparticle, $\chi_p$ denotes initial mass susceptibility of the magnetic nanoparticle, and $\chi_f$ denotes initial mass susceptibility of external environment. The above two kinds of forces may be applied simultaneously to the magnetic structure in the magnetic field that is not uniform.

The magnetic structure including the magnetic nanoparticles may be manufactured by various methods.

According to an embodiment, a method of manufacturing a color-coded magnetic structure using an OFML technique is provided. The above method includes: filling a microfluidic channel with a composition including a curable material and magnetic nanoparticles dispersed in the curable material; forming a one-dimensional chain structure of the magnetic nanoparticles by applying a magnetic field to the composition in the microfluidic channel; and forming free-floating particles in which the one-dimensional chain structure is fixed by irradiating patterned UV rays to the composition. By irradiating the patterned UV rays sequentially to the composition flowing in the microfluidic channel with changing a mask pattern, the composition may be multi-color-coded. Each of the free-floating particles manifesting structural colors may include a plurality of color dots. Each of the plurality of color dots may have a color determined according to the intensity of the magnetic field at the cured time. The color of the free-floating particle is determined according to the intensity of the magnetic field at the time of curing operation, and the shape and color pattern of the free-floating particle may be fixed by the pattern of the UV rays.

Figure 4:
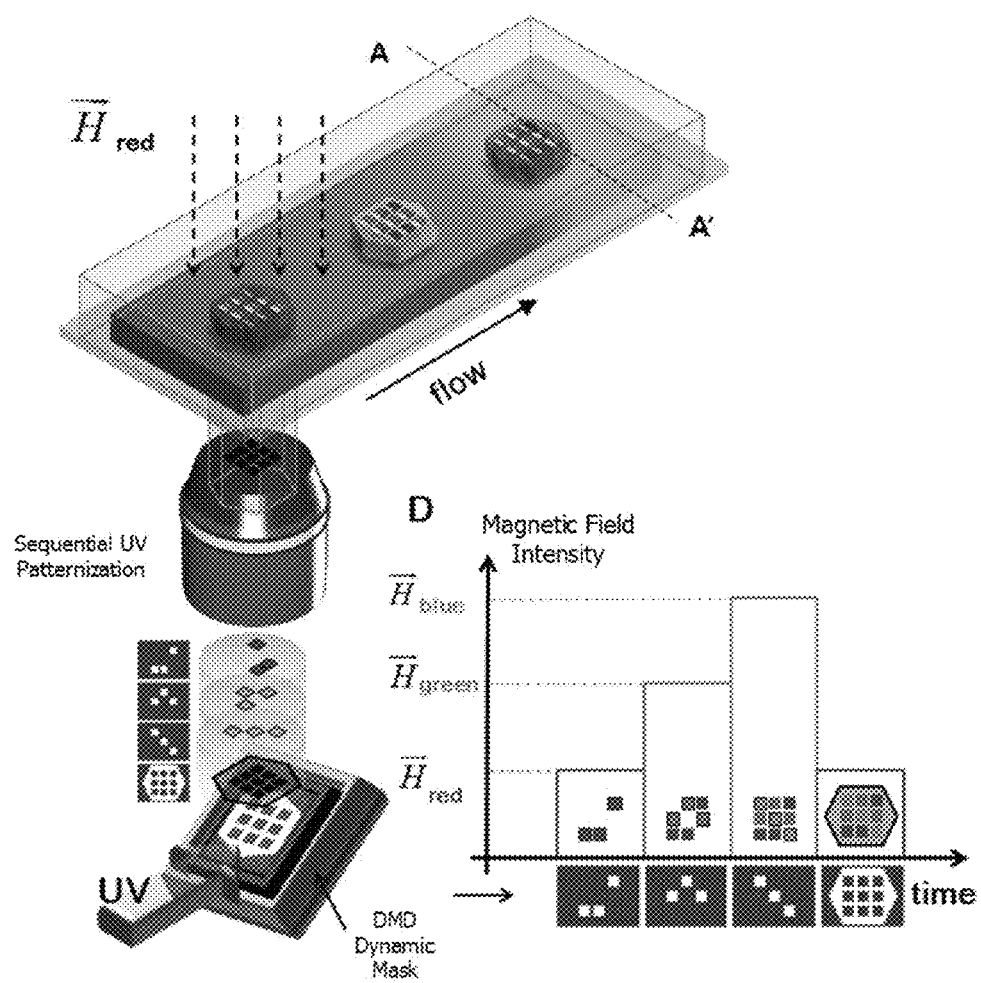
FIG. 4 is a schematic diagram showing generation of a multicolor-coded magnetic structure.

FIG. 4 is a schematic diagram showing processes of generating a multicolor-coded magnetic structure. Sequential processes including cooperative operations of magnetic field adjustment and spatially controlled UV exposure are used. First, a composition including a photocurable resin and super-paramagnetic nanoparticles dispersed in the photocurable resin is prepared. Next, a polydimethylsiloxane (PDMS) channel is filled with the above composition. Then, the color of the composition is tuned by adjusting an external magnetic field. A period of the one-dimensional (1D) chain structure formed by the super-paramagnetic nanoparticles is changed according to the intensity of the magnetic field, and light having a corresponding wavelength is reflected. Once a certain color code is induced in the composition by the external magnetic field, a locally patterned UV ray is irradiated to a partial region of the composition. A DMD, without a physical mask, may be used to irradiate the patterned UV ray. The DMD functions as a computer controlled spatial light modulator. In FIG. 4, the patterned UV ray is generated by the UV ray reflected from DMD. By irradiating the patterned UV, a partial region of the composition is coded to represent a certain color. Next, next code bits may be generated successively by simply changing the intensity of the magnetic field and changing the pattern of the DMD. According to the above color tuning and fixing processes, it takes about a tenth of a second to generate each bit, and thus the tuning and fixing processes may be performed rapidly. In addition, whenever each of the colors is induced, there is no need to perform a re-arrangement process that has to be performed in a process using a general mask, and thus, the process may be performed simply. Moreover, an oxygen lubricant layer, that is, an inhibition layer, in the PDMS channel allows microparticles generated by a radical polymerization to move along with the flow stream without sticking onto a channel wall.

By using the above properties, magnetic structures that are coded as various colors and shapes under an environment where the patterned UV rays and multiple levels of intensities of the magnetic field are applied may be generated by an OFML. That is, after injecting a liquid curable resin including photonic crystals into a microfluidic channel, an in-situ polymerization induced by the patterned UV rays under the magnetic field of multi-levels is performed to manufacture the magnetic structures. The magnetic structures may be designed to have arbitrary desirable shapes, and not limited to polygonal shapes. Heterogeneous coded magnetic structures including small color dots may be manufactured by being sequentially exposed to the UV rays under a multi-level magnetic field. In this case, there is no limitation in representing graphical codes owing to flexibility to colors and shapes.

According to an embodiment of the present invention, a color-coded magnetic structure including a solid medium and a magnetic axis in which magnetic nanoparticles are arranged at predetermined intervals therebetween in the solid medium is provided. The color-coded magnetic structure includes code regions manifesting structural colors due to light diffraction according to the interval between the arranged magnetic nanoparticles, and accordingly, the magnetic structure may be color-coded in multi-levels.

Figure 5:
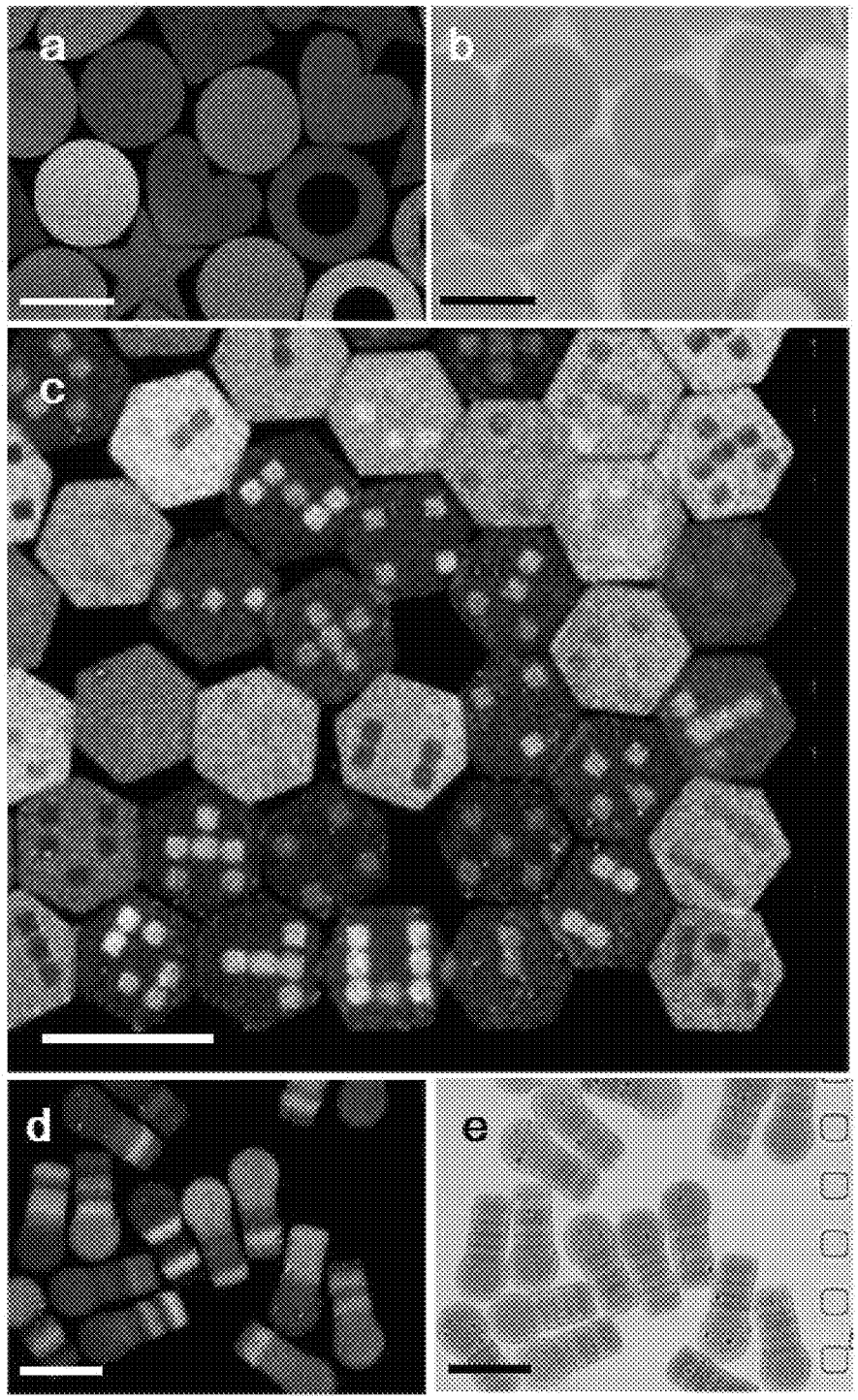
FIGS. 5A through 5E are images showing examples of color-coded magnetic structures in various types.

FIGS. 5A through 5E are images showing examples of color-coded magnetic structures in various types. Scale bars of FIGS. 5A and 5B are 200 µm each, a scale bar of FIG. 5C is 500 μm, and scale bars of FIGS. 5D and 5E are 250 μm each. As shown in FIGS. 5A, 5C, and 5D, magnetic structures having various shapes and various colors may be manufactured. FIGS. 5B and 5E are transmission electron microscope (TEM) images of samples shown in FIGS. 5A and 5D, respectively. Unlike FIGS. 5A and 5D showing colorful reflected images, FIGS. 5B and 5E show brown transmission images which represent that the color of the magnetic structure is caused by the structure of a superparamagnetic nanomaterial and not by coloring.

According to the above color coding operation, a plurality of colors are disposed in local spaces that are separated independently from each other. Also, a spectrum of the structural color in the local space has a single peak value. Therefore, information about location and color of each code may be obtained simultaneously from location information and RGB information of a pixel by using a charge coupled device (CCD) camera that is cheap.

The color-coded magnetic structure includes magnetic axes therein, and may be magnetically controlled by an external magnetic field. According to an embodiment of the present invention, a solution containing a magnetic structure including magnetic axes in which magnetic nanoparticles are arranged is provided. Next, movement of the magnetic structure is controlled by changing the external magnetic field with respect to the solution. Here, the movement may be caused by a rotating force generated by a magnetic torque of the magnetic axes or a translational force generated by a force applied in a direction in which density of the external magnetic field becomes dense. If probe molecules exist on a surface of the magnetic structure, the external magnetic field may be rotated in order to accelerate reaction between the probe molecules and object molecules in the solution. Here, the magnetic structure is rotated together with the magnetic field so as to increase collision frequencies between the probe molecules and the object molecules in the solution, thereby accelerating the reaction.

Also, information of the color codes may be easily analyzed through the magnetic control of the color-coded magnetic structure. According to an embodiment of the present invention, there is provided a method of magnetically controlling a magnetic structure including: introducing a solution containing magnetic structures that are color-coded by arranging magnetic nanoparticles in a container; and collecting the color-coded magnetic structures on a wall surface of the container by applying an external magnetic field to the solution; and analyzing information of the color codes, wherein surfaces, on which the color codes are located, of the magnetic structures are arranged two-dimensionally with respect to the wall surface of the container.

Figure 6:
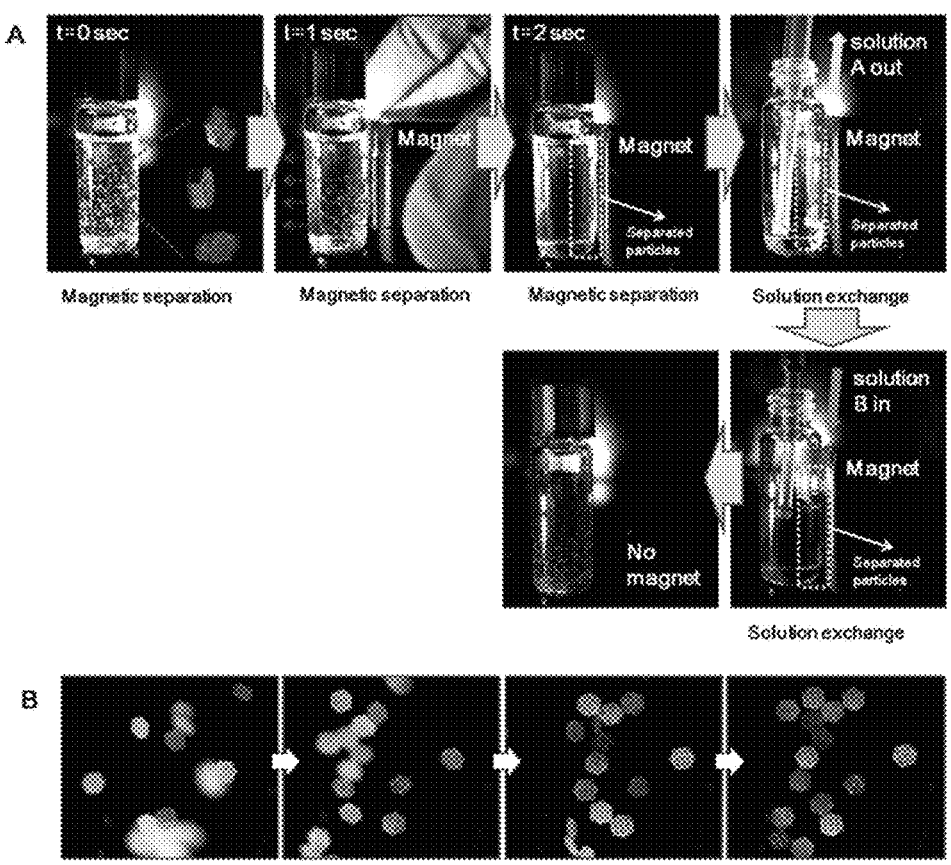
FIGS. 6A and 6B are diagrams showing processes of magnetically isolating color-coded magnetic structures and replacing a solution.

FIGS. 6A and 6B show processes of magnetically isolating the color-coded magnetic structures and replacing the solution. Referring to FIG. 6A, a magnet is located for a few seconds adjacent to a vial including a solution A containing color-coded magnetic structures such that the magnetic structure particles are collected on a wall of the vial, and then, solution A is replaced with a solution B. A final velocity of the magnetic structures may be about 4 mm/sec in consideration of a hydrodynamic drag force and the magnetic force. The time taken to reach the final velocity is ignorable when it is compared with an entire time for replacing the solution.

Referring to FIG. 6B, movements of the magnetic structures according to time after applying the external magnetic field are shown. When the magnetic field is applied to the solution, magnetic axes are arranged in parallel with magnetic force lines, and the magnetic structures may be magnetically dragged toward the wall of the vial. Since the magnetic axes are oriented in a thickness direction of the magnetic structures that are formed as flat plates, coded regions may be displayed two-dimensionally with respect to a surface of the vial wall. Therefore, the codes may be easily read only by focusing the surface of the vial by using a camera.

Figure 7:
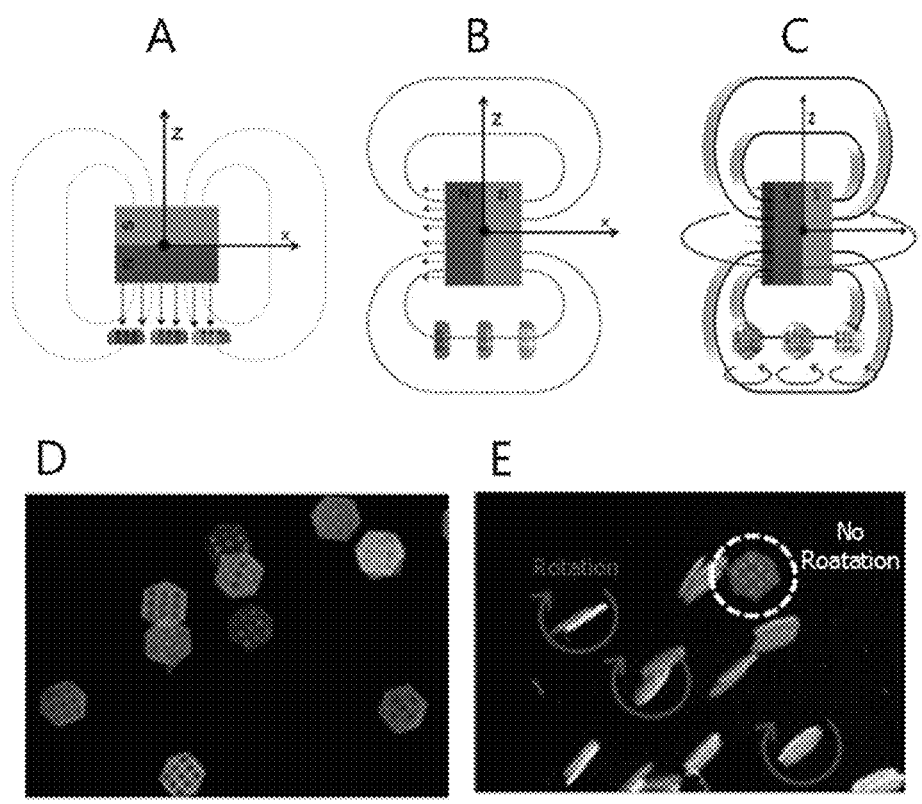
FIGS. 7A through 7E are schematic diagrams showing magnetic control of magnetic nanoparticles by using a magnet rotation setup, and microscope images of actual particles.

FIGS. 7A through 7E are schematic diagrams showing magnetic control of magnetic nanoparticles by using a magnet rotation setup, and microscope images of actual particles. FIG. 7A shows movements of microparticles when codes of the microparticles that are attached horizontally to a micro channel or a vial are read, or a solution is replaced. FIG. 7B shows flipping of the microparticles. Rotation of a magnet based on a Y-axis (perpendicular to an XZ plane of FIG. 7B) changes the direction of the magnetic force lines vertically across the microparticles. FIG. 7C shows rotating movements of the microparticles due to the rotation of the magnet based on a Z-axis.

In FIGS. 7A and 7B, the rotation about the Y-axis may make the microparticles attached to the micro channel for performing the code reading or the solution replacement, or the microparticles stand perpendicularly to the flow in order to accelerate reaction. Meanwhile, in FIGS. 7B and 7C, the rotation about the Z-axis makes the microparticles tumble around the Z-axis so as to increase a reaction region effectively. Next, processes of replacing the solution with a new solution for generating new reaction, activating the reaction by rotating the external magnetic field, and reading codes by attaching the microparticles on the surface of the vial after completing the reaction may be performed repeatedly.

FIG. 7D is a reflection type microscope image of coded particles placed under vertical magnetic force lines. FIG. 7E is an image showing rotation of the coded particles.

The color-coded microparticles may be arranged in parallel with the surface of the vial as shown in FIG. 7D, or may be stood upright as shown in FIG. 7E, according to the direction of the external magnetic force lines. When the microparticles are located in parallel with the surface of the vial, it is easy to read the coded colors. In FIG. 7E, horizontal external magnetic force lines that are rotating make the vertically arranged coded particles rotate around a vertical axis thereof, such that the rotation of the coded particles maximizes reaction between probes and targets in the solution. In FIG. 7E, a microparticle that does not rotate is a microparticle that is intentionally fabricated to contain magnetic nanoparticles that are randomly dispersed. The microparticle that does not rotate does not manifest a structural color, but shows the original brown color. On the other hand, microparticles that are rotating contain magnetic nanoparticles having one-dimensional chain structure. Thus, the magnetic axis including the magnetic nanoparticles with the one-dimensional chain structure allows the microparticle to rotate.

As described above, the magnetic structures including the magnetic axes may be multi-axis controlled, that is, flipping and rotating, when compared with general magnetic beads.

Figure 8:
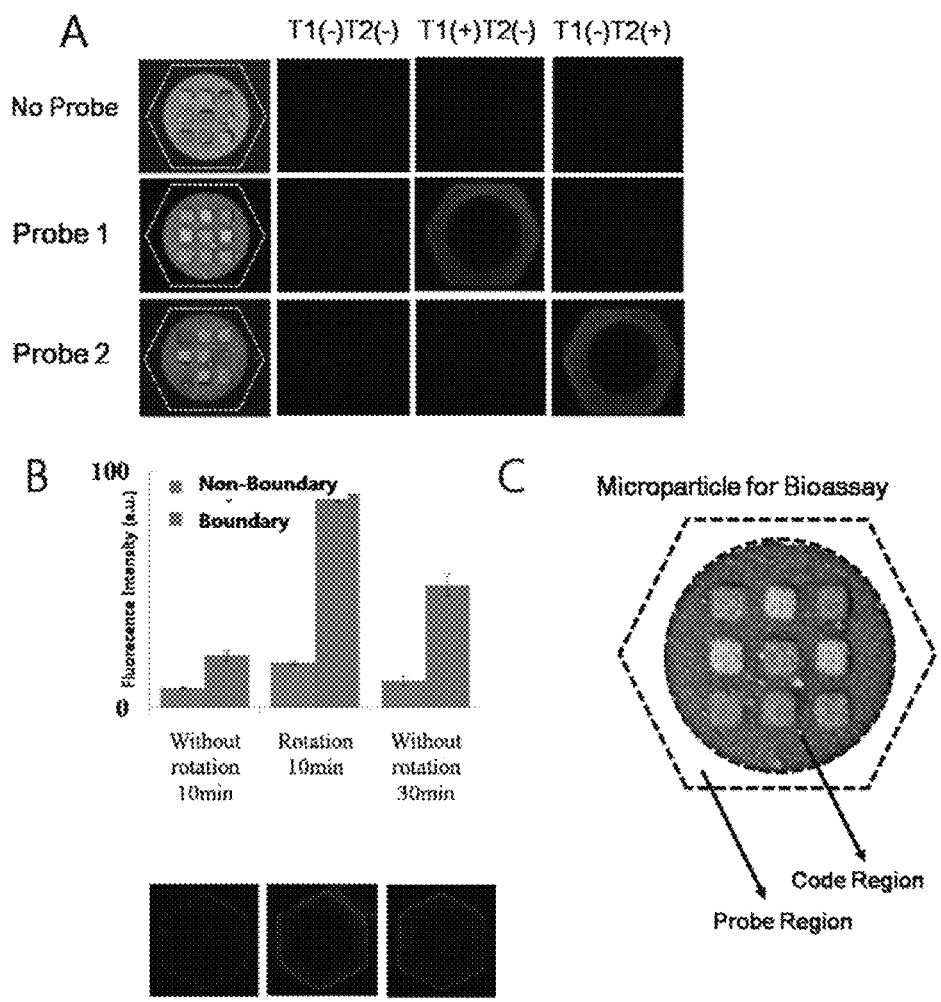
FIGS. 8A through 8C are diagrams showing an example of performing experiments for detecting and identifying DNA hybridization by controlling a color-coded magnetic structure.

FIGS. 8A through 8C show examples of performing experiments for detecting and identifying DNA hybridization by controlling a color-coded magnetic structure. As shown in FIG. 8C, a color-coded particle may include a code region and an oligonucleotide probe region. The oligonucleotide probe region is isolated from the code region in order to prevent a spectrum of a phosphor signal for detecting hybridization and a spectrum of a structural color signal for performing the color coding from overlapping each other. The code region is combined from a composition for fabricating a color-coded magnetic structure, and the probe region is formed of a compound of PEG-DA and a buffer solution of a DNA oligomer probe that is acrylate-modified.

As shown in FIG. 8A, DNA probes of 12.5 µM having various nucleotide sequences (probe 1: 5'-ACA CTC TAC AAC TTC-3', probe 2: 5'-ATC AGA TTG GTT AGT-3', and no DNA probe as a reference standard) were introduced in microparticles that are coded in multiple colors. DNA oligomer targets of 1 µM that are labeled by phosphor materials were introduced and cultivated for ten seconds. T1 and T2 are complementary targets of the probe 1 and the probe 2 respectively, mark (+) represents that the target exists and mark (−) represents that the target does not exist. Then, particles having the DNA probes that are complementary with the DNA oligomer targets only showed fluorescent.

Since the conventional magnetic beads contain magnetic materials that are randomly dispersed therein, there is a limitation in controlling movements of the magnetic beads. In more detail, in a case of the magnetic bead containing magnetic materials that are randomly dispersed, a drag force by the magnetic force line may be only applied, and forces of rotating a magnetization direction of each magnetic material by a force of the external magnetic field may be averaged and extinguished. On the other hand, in the microparticle including the magnetic axis, since the one-dimensional chain structure is formed, forces to make magnetization directions of the magnetic nanoparticles coincide with the direction of the external magnetic field are summed to be applied as a force to make all the particles move in that direction. The movements of the particles may be controlled by using the above property. For example, the microparticles including the magnetic axis may operate in cooperation with each other as millions of micro-scale rotating agitators. As shown in FIG. 8B, when reactions were actually generated by using the rotation of the magnetic microparticles through the magnetic control, reactivity of biomaterial reactions was increased because contacts to peripheral materials were increased by the rotation of the microparticles. Fluorescence intensity at a boundary of the microparticle probe region when the microparticles and DNA reacted with each other for ten minutes while rotating the magnetic microparticles increased four times greater than that when the microparticles and the DNA reacted with each other for ten minutes without rotating the microparticles. The increase in the reactivity as described above was much greater than the reactivity when the reaction is performed for thirty minutes without rotation.

The above described example is an example regarding the detection and identification of the DNA hybridization; however, the embodiment of the present invention may be applied to various biomolecules.

According to an embodiment, a biochemical analyzing method through reaction between probe molecules and target molecules in a magnetic structure of emulsion type may be performed by magnetically controlling the magnetic structure. To do this, a composition of magnetic nanoparticles dispersed in a curable medium is dispersed in an immiscible solvent to form emulsion. Next, a magnetic field is applied to the emulsion and light is irradiated to manufacture a magnetic structure of a microsphere type including a magnetic axis. Probe molecules are immobilized on a surface of the magnetic structure for performing a biochemical analysis. The magnetic structure is mixed in a solvent containing target molecules. An external magnetic field is applied to the magnetic structure so as to rotate or move the magnetic structure on which the probe molecules are immobilized, thereby accelerating reaction with the target molecules. After completing the reaction, the magnetic structure is collected by applying an external magnetic field having an inclined intensity so as to isolate the magnetic structure from the solvent.

According to an embodiment, a magnetic control device configured to perform biochemical analysis by magnetically controlling a magnetic structure is provided.

Figure 9:
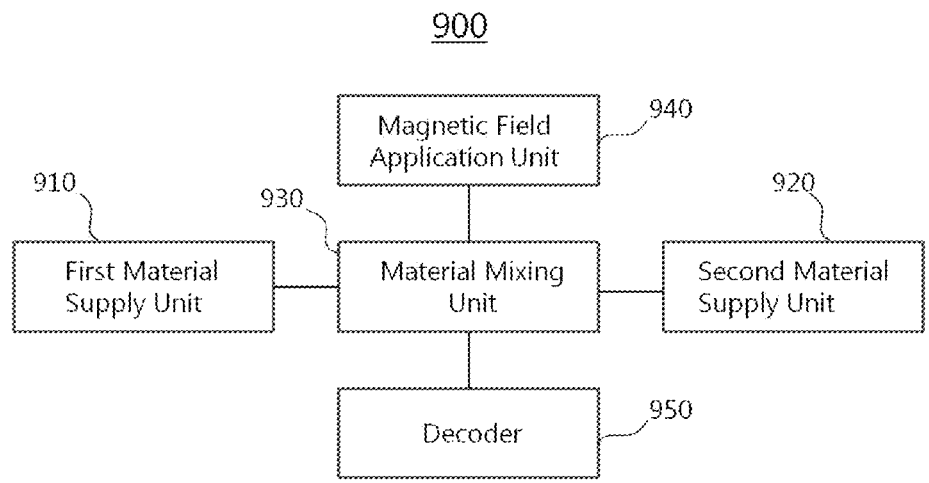
FIG. 9 is a block diagram showing a device for magnetically controlling a magnetic structure configured to perform a biochemical analysis according to an embodiment of the present invention.

FIG. 9 shows a device for magnetically controlling a magnetic structure configured to perform a biochemical analysis according to an embodiment. Referring to FIG. 9, the magnetic control device of a magnetic structure 900 includes a first material supply unit 910, a second material supply unit 920, a material mixing unit 930, a magnetic field application unit 940, and a decoder 950.

The first material supply unit 910 stores and supplies magnetic structures as a material. The magnetic structure is color-coded by arranging magnetic nanoparticles, and includes probe molecules.

The second material supply unit 920 stores and supplies a solution containing target molecules.

The material mixing unit 930 is a space where the magnetic structures and the solution are mixed so that the probe molecules and the target molecules react with each other.

The magnetic field application unit 940 applies a magnetic field to the solution so as to rotate or move the magnetic structures in the solution. The magnetic field application unit 940 includes a magnet that is movable and has an adjustable magnetic force for varying the magnetic field. The reaction between the materials may be accelerated by the application of the magnetic field.

The decoder 950 observes and decodes the magnetic structures on which the probe molecules and the target molecules are combined with each other. The decoder 950 includes a CCD camera so that information about location and color of each code may be obtained simultaneously from location information and RGB information of each pixel that is obtained through a capturing operation. The magnetic field application unit 940 may apply a magnetic field to the magnetic structures to collect the magnetic structures, and then the decoder unit 950 may observe the magnetic structures.

The magnetic structure having the magnetic axis may be a structure having a multi-directional magnetic axis, besides the color-coded microparticle.

According to an embodiment, a magnetic structure is provided. The magnetic structure may include a solid matrix; a first region located on a portion of the solid matrix and including a fixed magnetic axis; and a second region located on another portion of the solid matrix to be connected to the first region and including a fixed magnetic axis. Here, orientation of the magnetic axis in the first region and orientation of the magnetic axis in the second region differ from each other. Also, when an external magnetic field is applied, the first region and the second region may move differently from each other due to heterogeneous magnetic anisotropy of the magnetic axis in the first region and of the magnetic axis in the second region. The solid matrix may be formed of a polymer material. As described above, when the magnetic structure includes the magnetic axes formed in different directions, a micro actuator moving in different directions under a uniform magnetic field may be realized.

At least a portion of the solid matrix may be fixed on an external material. For example, at least a portion of the solid matrix may be fixed on an inner wall of a microfluidic channel. In this case, a micro actuator of a cantilever type may be realized.

Figure 10:
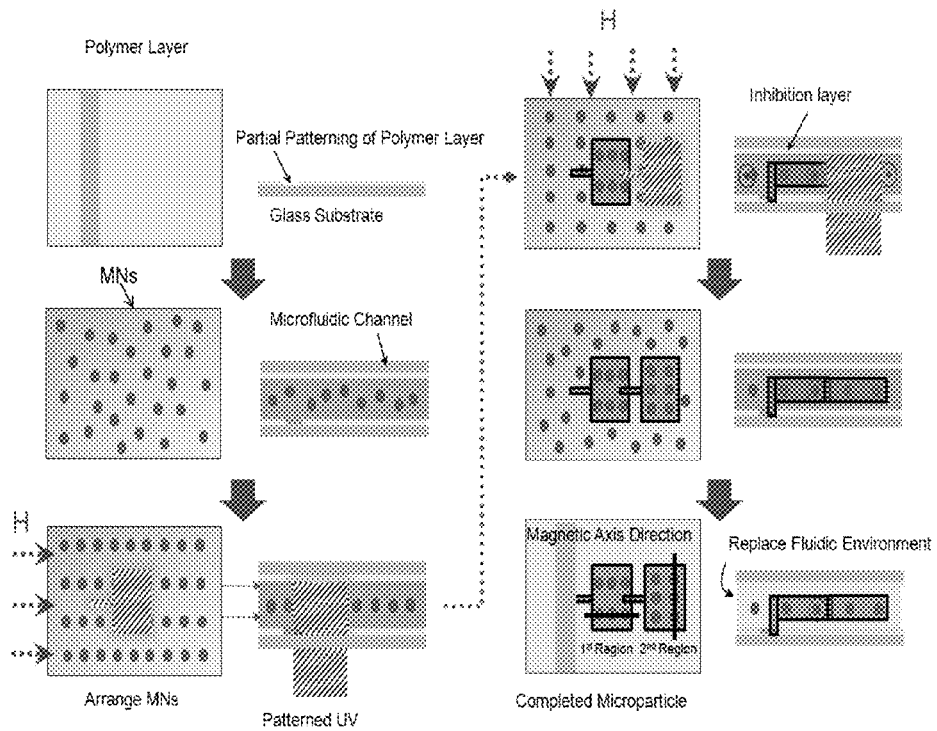
FIG. 10 is a diagram showing processes of manufacturing a polymer microstructure including multi-directional magnetic axes.
Figure 11:
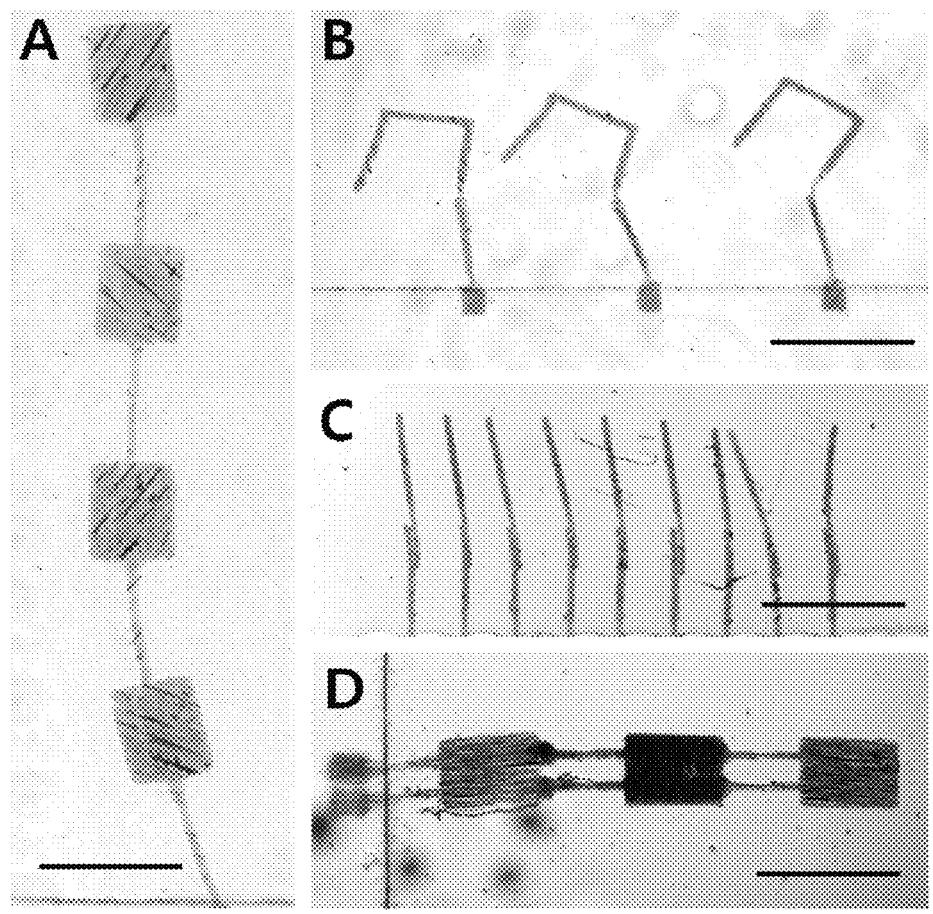
FIGS. 11A through 11D are images showing examples of microstructures including magnetic nanoparticles arranged in multi-directions in various types.

FIG. 10 is a diagram showing processes of manufacturing a polymer microstructure including multi-directional magnetic axes. In each process, a left portion shows a front view and a right portion shows a side-sectional view. Experimental equipment includes an OFML device capable of manufacturing polymer microstructures of various shapes without using a mask, and a permanent magnet configured to generate and adjust an external magnetic field. Sequential processes are performed by using the experimental equipment. First, a glass substrate is coated by a polymer material that forms an inhibition layer configured to prevent a part of the microparticle from being attached to the substrate. Then, a desired portion of the coating material is removed in order to attach a part of the microparticle to the glass substrate coated with the polymer material. In addition, a microfluidic channel is attached thereon, and liquid in which a curable material and magnetic nanoparticles are mixed is filled in the microfluidic channel. When a uniform magnetic field is formed across the microfluidic channel, the magnetic nanoparticles form chains of the nanoparticles along a direction of magnetic force lines. In this state, the liquid is photocured to be a desired shape within a short period of time while fixing the chains in a part of the fluid by using the OFML system that does not use a mask, and thus, a first region in which the magnetic axis is fixed in a desired direction is formed. After the curing process, the direction of the magnetic field is changed, and the liquid having a magnetic axis in a direction that is the same as the newly changed direction of the magnetic field is photocured to form a second region. The above resetting process of the magnetic force line direction and the fixing process through the polymer photocuring are repeatedly performed until the microstructure is completely formed. After manufacturing of the structure is finished, the remaining liquid is changed to a liquid that is suitable for controlling the microstructure. The above method may be performed much faster than a thermosetting method, and thus, states of the nanoparticles that are self-assembled in various ways may be fixed in the polymer with high resolution. Accordingly, a microstructure including the multi-directional magnetic nanoparticles may be completely manufactured within a short period of time.

FIGS. 11A through 11D are images showing examples of microstructures including magnetic nanoparticles arranged in multi-directions in various types. Scales bars denote 200 μm. As shown in FIGS. 11A through 11D, a polymer microstructure having various magnetic axes within a structure may be easily manufactured to have various shapes. The polymer microstructure manufactured by the above method may be magnetically controlled to have complicated movements, beyond the limitations in control that are shown by the conventional polymer microstructure.

Figure 12:
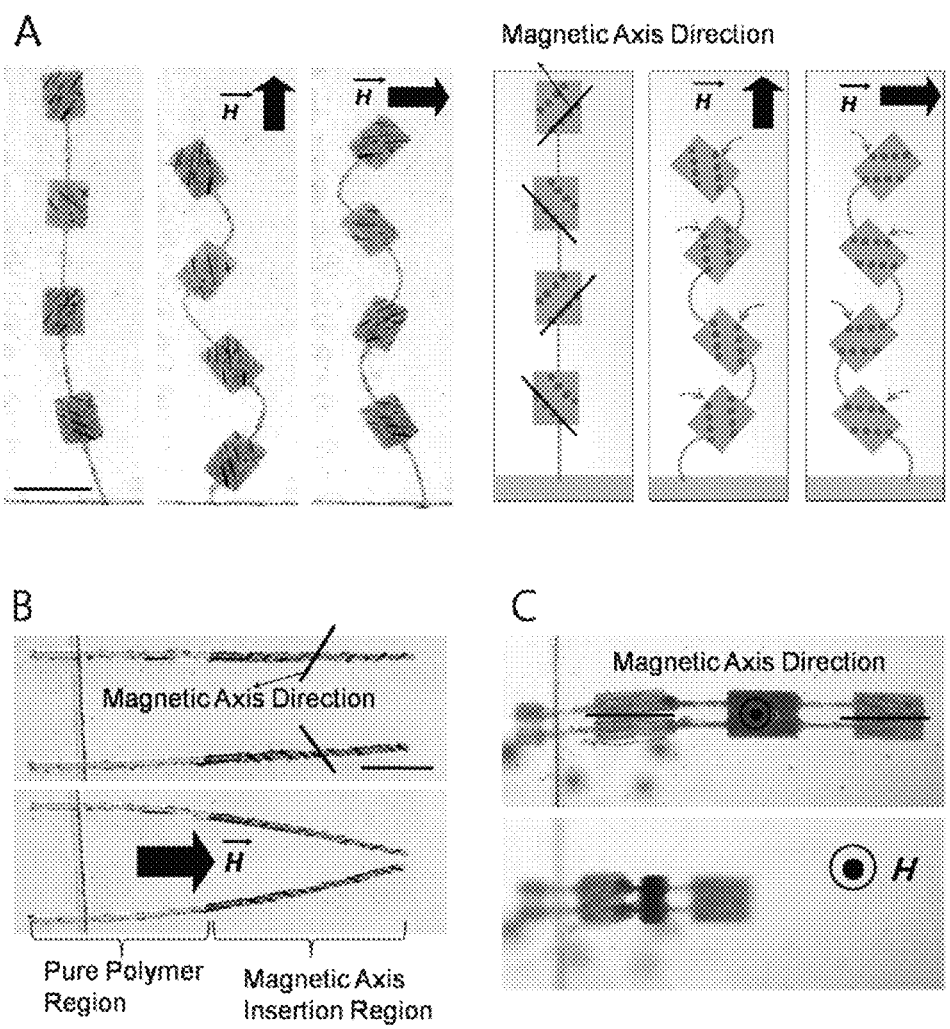
FIGS. 12A through 12C are diagrams showing results of realizing various movements by applying a uniform magnetic field to a microstructure including multi-directional magnetic axes.

FIGS. 12A through 12C show results of realizing various movements by applying a uniform magnetic field to a microstructure including multi-directional magnetic axes. The microstructure shown in FIG. 12A includes a chain of magnetic nanoparticles formed in four directions that are perpendicular to each other. When an external magnetic field is applied to the microstructure of FIG. 12A, rotating forces are applied to each of the portions in the microstructure in different directions, and accordingly, new movements that may not be observed in the conventional microstructure are shown. Since the microstructure may be formed to have various shapes by using the OFML and a direction of the magnetic nanoparticle chain may be freely set, various movements may be realized as shown in FIGS. 12B and 12C without regard to whether the magnetic nanoparticles are arranged in a two-dimensional (2D) or three-dimensional (3D) way.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of magnetically controlling a magnetic structure, the method comprising:
    providing a magnetic structure including a solid matrix having a first region and a second region directly connected to the first region via a connecting region, each of the first and the second regions including magnetic axes,
    wherein each of the magnetic axes includes magnetic nanoparticles arranged along an axial direction in a linear line with a predetermined interval therebetween and fixed in each region, and
    wherein the connecting region is bent between the first and the second regions when an external magnetic field is applied to allow the first and the second regions to move in different directions by the applied external magnetic field; and
    controlling movements of the magnetic structure by i) applying an external magnetic field to the magnetic structure and ii) changing a direction of the applied external magnetic field, such that the first and the second regions in the magnetic structure move in different directions from each other and the connecting region is bent.

2. The method of claim 1, wherein the solid matrix is made of a curable material.

3. A method of magnetically controlling and analyzing a magnetic structure, the method comprising:
    introducing into a container a solution containing a color-coded magnetic structure having a flat plate, the color-coded magnetic structure including code regions formed on a flat surface of the color-coded magnetic structure, each code region including magnetic axes oriented in a thickness direction of the color-coded magnetic structure which is perpendicular to the flat surface, each magnetic axis including magnetic nanoparticles arranged in an axial direction with predetermined intervals therebetween and fixed in each code region, the code regions manifesting structural colors due to light diffraction in accordance with the intervals between the magnetic nanoparticles arranged in each code region;
    controlling movements of the color-coded magnetic structure in the container by applying an external magnetic field to the solution from an outside of the container, the external magnetic field enabling the color-coded magnetic structure to rotate by creating a magnetic torque to the color-coded magnetic structure and to move translationally by creating a force applied in a direction in which a density of the external magnetic force becomes dense;
    collecting the color-coded magnetic structure in the solution on a wall surface of the container by applying an external magnetic field to the solution such that the flat surface of the color-coded magnetic structure contained in the solution is dragged toward the wall surface of the container and the code regions manifesting structural colors are displayed to an outside of the container through the wall surface of the container; and reading information of the code regions by using a camera focusing the wall surface of the container.

4. The method of claim 3, further comprising exchanging the solution in the container for another solution which is different from the solution, while the color-coded magnetic structure is collected on the wall of the container by the applied external magnetic field.

5. The method of claim 3, wherein the magnetic nanoparticles are fixed in a cured material.

6. The method of claim 3, wherein the color-coded magnetic structure further includes an oligonucleotide probe region isolated from the code regions, wherein the oligonucleotide probe region is formed of a compound of PEG-DA and a buffer solution of a DNA oligomer probe that is acrylate-modified.

7. The method of claim 3, wherein probe molecules exist on the flat surface of the color-coded magnetic structure, and the color-coded magnetic structure is rotated according to rotation of the external magnetic field to accelerate reaction between the probe molecules and target molecules in the solution.

8. The magnetic structure of claim 1, wherein the connecting region is made of a photo-curable polymer material.

* * * * *